United States Patent [19]

Denzinger et al.

[11] 4,320,114

[45] Mar. 16, 1982

[54] MANUFACTURE OF AQUEOUS POLYVINYLPYRROLIDONE-IODINE SOLUTIONS

[75] Inventors: Walter Denzinger, Speyer; Karl Herrle, Ludwigshafen; Hans-Uwe Schenck, Frankenthal, all of Fed. Rep. of Germany

[73] Assignee: BASF Aktiengesellschaft, Fed. Rep. of Germany

[21] Appl. No.: 181,802

[22] Filed: Aug. 27, 1980

Related U.S. Application Data

[63] Continuation of Ser. No. 961,706, Nov. 17, 1978, abandoned, which is a continuation of Ser. No. 876,988, Feb. 13, 1978, abandoned, which is a continuation of Ser. No. 710,426, Aug. 2, 1976, abandoned.

[30] Foreign Application Priority Data

Sep. 10, 1975 [DE] Fed. Rep. of Germany ....... 2540170

[51] Int. Cl.$^3$ .............................................. A61K 31/79
[52] U.S. Cl. ....................................................... 424/80
[58] Field of Search .......................................... 424/80

[56] References Cited

U.S. PATENT DOCUMENTS 2,826,532  3/1958  Hosmer ................... 424/80
2,900,305  8/1959  Siggia ..................... 424/80
4,027,083  5/1977  Herrle et al. ........... 526/23

*Primary Examiner*—Frederick E. Waddell
*Attorney, Agent, or Firm*—Keil & Witherspoon

[57] ABSTRACT

Aqueous solutions of polyvinylpyrrolidone-iodine, generally referred to as PVP-iodine, which is finding increasing use because of its germicidal, bactericidal, fungicidal and disinfectant properties.

11 Claims, No Drawings

MANUFACTURE OF AQUEOUS POLYVINYLPYRROLIDONE-IODINE SOLUTIONS

This is a continuation, of application Ser. No. 961,706, filed Nov. 17, 1978, now abandoned, which is a continuation of Ser. No. 876,988, filed Feb. 13, 1978, now abandoned, which is a continuation of Ser. No. 710,426, filed Aug. 2, 1976, now abandoned.

The present invention relates to aqueous solutions of polyvinylpyrrolidone-iodine, generally referred to as PVP-iodine, which is finding increasing use because of its germicidal, bactericidal, fungicidal and disinfectant properties.

PVP-iodine is generally marketed as a brown powder which contains about 10% of available, ie. active, iodine, which can be titrated with sodium thiosulfate, and in addition contains about 5% of iodine in the form of iodine ions. The iodide ion present is produced wholly or at least partially by the action of elementary iodine on the polyvinylpyrrolidone. However, iodide ions can also in part be added to the product, before or after the addition of iodine, in the form of compounds which provide iodide ions.

In the manufacture of PVP-iodine, the procedure generally followed is first to mix pulverulent polyvinylpyrrolidone thoroughly with powdered iodine in a mixer, until the iodine as such has disappeared, ie. has dissolved, or been bound as a complex, in the PVP. The powder is then heated for several hours at about 100° C. The result of this is that the content of available iodine remains constant on storage.

According to another process, the iodine is dissolved in a solvent which does not dissolve polyvinylpyrrolidone, the polyvinylpyrrolidone is admixed and the PVP-iodine which precipitates is separated off.

The formulations intended for the ultimate consumer can be prepared from the pulverulent PVP-iodine by conventional methods, using the conventional pharmaceutical assistants; these formulations are, in general, aqueous solutions which can contain additional assistants, eg. surfactants, alcohol, glycerol and buffers.

German Pat. No. 902,170 discloses that a Lugol solution can be combined with PVP. As is known, Lugol solution is an aqueous solution which contains iodine and potassium iodide in the ratio of 1:2. Such solutions have the disadvantage that if they are prepared from commercial PVP, which is usually manufactured according to German Pat. No. 922,378, by polymerizing vinylpyrrolidone in aqueous solution in the presence of hydrogen peroxide, the content of active iodine rapidly drops on storage. The stability of aqueous PVP-iodine solutions which have been prepared by dissolving solid PVP-iodine in water, the PVP-iodine having been obtained from solid PVP and iodine with or without the addition of iodide, at elevated temperatures, is significantly better.

We have now found that a process for the manufacture of stable aqueous solutions of PVP-iodine by mixing PVP, iodine and a compound which provides iodide ions in an aqueous medium, in which process a PVP which has been polymerized in organic solution, using organic initiators, is employed.

According to the invention, the components are mixed in water as the solvent. However, up to 50% of other solvents, which are water-miscible, preferably ethanol or isopropanol, may be used.

The PVP to be used according to the invention advantageously has a K value of from 8 to 50, especially from 10 to 35 and preferably from 10 to 25. It is manufactured by polymerization in an organic solvent in the presence of organic initiators and, if appropriate, also in the presence of a complex compound of a heavy metal of atomic number from 23 to 29 or of its salt with an organic acid, as co-activator.

Suitable organic solvents are aromatic hydrocarbons, especially toluene, and lower aliphatic monohydric alcohols, especially of 1 to 4 carbon atoms, eg. ethanol, propanol and isopropanol.

Organic initiators used are organic per-compounds, especially alkyl hydroperoxides and dialkyl peroxides of 1 to 8 carbon atoms per alkyl, eg. tert.-butyl hydroperoxide and di-tert,-butyl peroxide, and per-esters, eg. tert.-butyl pivalate. Of these, di-tert.-butyl peroxide is particularly preferred.

The amount of the organic per-compounds may vary within wide limits and depends on the molecular weight which is to be obtained. In general, the amounts required are from 0.1 to 5%, based on the weight of the vinylpyrrolidone.

It is frequently advantageous to add a complex compound or a salt, with an organic acid, of a heavy metal of atomic number from 23 to 29 as a coactivator.

The heavy metals of atomic number from 23 to 29 are vanadium, chromium, manganese, iron, cobalt, nickel and copper. These compounds are extremely active and are used in very small amounts, advantageously of from 0.01 to 10 ppm, preferably from 0.1 to 5 ppm, based on the weight of the vinylpyrrolidone. Amongst the stated heavy metals, copper is preferred.

Organic acids which may be used to form the salts are aliphatic carboxylic acids of 2 to 18 carbon atoms, eg. acetic acid, ethylhexanoic acid and stearic acid, and aromatic acids, eg. benzoic acid and phenylacetic acid.

The heavy metals can also be employed in the form of chelate complexes or in the form of other complexes. Suitable complex-forming agents, are, eg., $\beta$-diketones, such as acetylacetone, hydroxyketones, such as hydroxyacetone, hydroxycarboxylic acids, such as lactic acid, citric acid and salicylic acid, and aminoacids, such as glycine or ethylenediaminotetraacetic acid.

The following heavy metal salts and complex compounds may be mentioned specifically: copper acetate, copper acetylacetonate, copper stearate, nickel glycinate, manganese-II salicylate and chromium-III benzoate.

The actual polymerization is carried out by conventional methods. The concentration of the monomer in the batch is from 10 to 80% by weight and preferably from 20 to 70% by weight. In general, all the components of the batch are introduced from the start. However, in many cases it may prove advantageous to run in one or more components during the polymerization. Advantageously, the air or oxygen contained in the solution is removed, before starting the polymerization, by applying reduced pressure or by flushing with nitrogen. The temperatures used are advantageously from 50° to 180° C. In general, polymerization is carried out at the boil under atmospheric pressure. The boiling point and hence the polymerization temperature can be varied within the limits by use of superatmospheric pressure or reduced pressure and by suitable choice of the solvent. The desired molecular weight or the desired K value are essentially obtained by suitable selection of the solvent, of the concentration of the batch, of the nature and amount of the activator and any coactivator, and of the polymerization temperature. Furthermore, it may depend on whether the monomer is entirely introduced at the start or is run in during the polymerization.

Solvents with a tertiary hydrogen atom in general give lower K values than those which only contain secondary or primary hydrogen atoms. An example is given by isopropanol and ethanol. Increasing the monomer concentration also increases the K value. Increasing amounts of activator and increasing polymerization temperature lower the K value. The K values were measured by the method of H. Fikentscher, Cellulosechemie 13 (1932), 58–64 and 71–74; K corresponds to the parameter k·$10^3$ defined by Fikentscher.

Polymers which have been manufactured using, as the initiator, an alkyl hydroperoxide or dialkyl peroxide of 1 to 8 carbon atoms in the alkyl, especially di-tert.-butyl peroxide, are particularly advantageous. These polymers carry at least one alkoxy end group originating from the initiator. For example, in the case of PVP manufactured using di-tert.-butyl peroxide, the signal of the tert.-butoxy end group in the polymer can be seen in the 22.63 Mc/s $^{13}$C nuclear resonance spectrum at 70 ppm relative to tetramethylsilane.

If the polymerization is carried out in a water-miscible solvent, for example a lower alcohol, such as ethanol or isopropanol, the polymer solution first produced can, after dilution with water, in many cases be employed directly for the preparation of aqueous PVP-iodine solutions. In general, however, it is advantageous to distil the organic solvent from the polymer solution after adding water, especially if water-immiscible solvents are used for the polymerization.

In many cases it is also particularly advantageous to follow this by a steam distillation, by blowing steam, advantageously in an amount of from 20 to 200% by weight based on the PVP, through the aqueous PVP solution which has been freed from organic solvent. If desired, the aqueous PVP solution can be dried in the usual way, preferably by spray-drying.

In preparing the aqueous PVP-iodine solution, it is advantageous to start from aqueous PVP solutions of from 10 to 60% strength by weight, with the higher concentrations applying to polymers of low K value and vice versa.

Commercial iodine, suitably in a finely ground form, is used to accelerate the dissolution. The amount of the iodine is from 5 to 60% by weight, preferably from 5 to 20% by weight, based on the amount of PVP employed.

Compounds which provide iodide ions are above all hydriodic acid and its ammonium, alkali metal and alkaline earth metal salts. Sodium iodide and potassium iodide are preferred. The amount to be used, calculated as iodide ions, is from 10 to 200% by weight, preferably from 30 to 80% by weight, based on the amount of iodine employed.

The aqueous PVP-iodine solutions are prepared in, eg., a conventional stirred kettle. Advantageously, a solution of PVP and of the compound which provides iodide ions is first prepared and the iodine is then added whilst stirring, in such a way as to avoid the formation of lumps. Depending on the intensity of stirring, a homogeneous solution is obtained in from about 2 to 6 hours.

A particularly advantageous variant of the process is that in place of elementary iodine, the compound which provides iodide ions, eg. sodium iodide or potassium iodide, is employed in excess, and the iodine is produced in situ by adding an oxidizing agent.

Suitable oxidizing agents for partially converting iodide ions into free iodine are, for example, iodine compounds which have an oxidizing action, eg. sodium hypoiodide, sodium iodate and iodine pentoxide. Per-compounds may also be used, eg. potassium persulfate, sodium percarbonate and organic per-compounds, eg. tert.-butyl hydroperoxide. However, hydrogen peroxide is preferred, since it produces no residues, other than water, during the oxidation.

In general, organic per-compounds oxidize the iodide ions slowly. It is therefore frequently advisable to add small amounts, in general from 0.01 to 10 ppm based on the total weight of the solution, of a complex compound of a heavy metal of atomic number from 23 to 29 or of a salt of such a metal with an organic or inorganic acid. In this way, the oxidation end-point can be reached substantially more quickly. The preferred heavy metal compounds are copper acetate and copper chloride.

The same effect can also be achieved if the temperature, which is usually about room temperature, is raised to values of up to 90° C.

For the purpose of the oxidation of the compound which provides iodide ions, it is advantageous to maintain an acid pH in the mixture. This is achievable, eg., by adding acids, such as citric acid or phosphoric acid, or acid buffer salts, such as monosodium phosphate.

The amounts of compound which provides iodide ions and of oxidizing agent are so chosen that the content of available iodine in the aqueous solution is from about 0.5 to 30% by weight and preferably from 0.5 to 5% by weight. From 0.2 to 30, preferably from 0.2 to 10, % by weight of iodide ions, eg. in the form of K iodide or Na iodide, may remain in the solution. To achieve this, the amounts of oxidizing agent used are in general from 40 to 200% of the amount theoretically required for the quantitative oxidation of the compound which provides iodide ions. Since the oxidizing agents, above all hydrogen peroxide, do not react quantitatively with the compounds which provide iodide ions, an excess of oxidizing agent is frequently added.

The pH of the PVP-iodine solution prepared according to the invention is advantageously from 2 to 7 and preferably from 4 to 6. It can be adjusted by adding buffer salts, sodium citrate, sodium bicarbonate and sodium pyrophosphate being preferred. In general, the amount of the buffer substance is from about 10 to 100%, based on the compound employed which provides iodide ions, and depends on the nature of the oxidizing agent employed and on the nature of the compound which provides iodide ions.

If, eg., hydrogen peroxide is used as the oxidizing agent and potassium iodide as the compound which provides iodide ions, it is necessary to add about an equivalent amount of acid, eg. citric acid or phosphoric acid, before or during mixing of the compounds, in order to obtain the desired pH of from 2 to 7, preferably from 4 to 6. If this is not done, the mixture begins to react alkaline and hydrogen peroxide decomposes, with elimination of oxygen, as becomes manifest from an evolution of gas. If, on the other hand, hydrogen peroxide and hydriodic acid, or potassium persulfate and potassium iodide, are used, only a slight correction of the pH is required.

The PVP-iodine solutions prepared according to the invention can be formulated in the conventional manner, with addition of further assistants, eg. surfactants, to give the end products intended for the consumer. These solutions in general have a total concentration of from 10 to 50% by weight of solids.

Using the process according to the invention, it is also possible to convert a pulverulent PVP into an aqueous PVP-iodine solution. However, it is particularly advantageous to start from the solutions obtained from the polymerization reaction.

Whilst in processes of the prior art, the first step is as a rule to obtain a pulverulent PVP, from the PVP solutions formed in the polymerization, by drying, and then to convert this, by reaction with iodine, into solid PVP-iodine, from which a solution is prepared by dissolving in water, it is possible, using the process according to the invention, to obtain PVP-iodine solutions in one step from the PVP solutions obtained from the polymerization, which solutions may, if necessary, first be flushed with steam.

A further advantage of the process is to be found in the embodiment in which the iodine required is produced in situ from a compound which provides iodide ions and an oxidizing agent.

This method makes it possible to circumvent the use of elementary iodine, which is not only volatile but also toxic. The use, according to the invention, of PVP polymerized in organic solution, using organic activators, makes it possible to prepare a product of substantially improved stability compared to those of the prior art.

Using the process described, it is possible to produce aqueous PVP solutions of good stability by a simple method, if desired circumventing the use of elementary iodine, which solutions can be formulated in a plurality of ways in the course of the same process step.

EXAMPLE 1

A. Comparative Example with PVP polymerized in aqueous solution:

Following the method of German Pat. No. 922,378, 400 parts of vinylpyrrolidone are dissolved in 1,600 parts of water and polymerized, using 8.4 parts of 30% strength hydrogen peroxide and 4 parts of aqueous concentrated ammonia solution, in a stirred kettle at 70° under a slight stream of nitrogen, until, after 4 hours, the residual content of monomeric vinylpyrrolidone, determined by the method of Siggia and Edsberg, has fallen to below 0.5%. The K value of the polymer is 30.4 and the solids content of the solution is 20%.

The solution is divided into 4 parts, which are then converted to aqueous PVP-iodine solutions as follows.

(a) A solution of 6.5 parts of potassium iodide in 70 parts of water is added to 412.5 parts, and 11 parts of ground iodine are then added with vigorous stirring. After stirring for 4 hours, the iodine has dissolved and the solution is homogeneous.

(b) 412.5 parts of the solution are flushed with 82.5 parts of steam and the solution is then treated further as described under (a).

(c) The solution is converted by spray-drying into a powder containing 8.1% of water. A 20% strength solution in water is then again prepared and is treated further as described in Example (a).

(d) The solution is spray-dried as described under (c). 92.4 parts of the solid product thereby obtained, containing 8.1% of water, are mixed with 15 parts of ground iodine in a tumbler mixer for 6 hours at room temperature and the mixture is then heated for 15 hours at 95° C. A solution is prepared by adding 393 parts of water.

The solutions obtained according to (a) to (d) are tested for their stability, as follows:

After determining the available iodine content, ie. the iodine content which can be titrated with sodium thiosulfate, the solutions are diluted to an available iodine content of 1.0% and stored in a closed ground-neck flask for 15 hours in an oven at 80°. After cooling, the loss of iodine which has occurred on storage is determined by recalculating the iodine content.

The following values were found:

| Experiment | Available iodine content % | Loss of iodine in 15 hours at 80° C. % |
|---|---|---|
| a | 2.04 | 60.6 |
| b | 2.05 | 54.1 |
| c | 2.07 | 48.5 |
| d | 1.95 | 12.5 |

B. 500 parts of vinylpyrrolidone, 214 parts of isopropanol and 5 parts of tertiary butyl hydroperoxide are boiled in a stirred kettle fitted with a reflux condenser. After the boiling point of 96° C. has been reached, 0.25 part of an 0.1% strength solution of copper acetylacetonate in isopropanol is added and the mixture is heated until the residual vinylpyrrolidone content is less than 0.5%, and is then diluted to 20% strength with 1,786 parts of water. The K value of the polymer is 30.4. The solution is divided into 4 parts, which are then converted to aqueous PVP-iodine solutions as follows.

(a) A solution of 6.5 parts of potassium iodide in 70 parts of water is added to 412.5 parts, and 11 parts of ground iodine are then added with vigorous stirring. After stirring for 4 hours the solution is homogeneous.

(b) The isopropanol is distilled from 412.5 parts of the solution by blowing steam into the mixture, and after the temperature at which the vapor passes over has reached 98° C., the mixture is flushed with a further 82.5 parts of steam. After bringing the PVP content to 20% with water, the solution is further treated as described under (a).

(c) The isopropanol is distilled from 500 parts of the solution by blowing steam into the mixture and after the temperature at which the vapor passes over has reached 98° C., the mixture is flushed with a further 100 parts of steam. The solution is then converted to a powder, containing 8.0% of water, by spray-drying. A 20% strength solution in water is then again prepared and this is treated further as described under Example (a).

(d) The solution is treated with steam as described under (c) and is spray-dried to give a powder containing 8.0% of water.

92.4 parts of the solid product thus obtained are mixed with 15 parts of ground iodine in a tumbler mixer for 6 hours at room temperature and then heated for 15 hours at 95° C. A solution is prepared by adding 393 parts of water.

The stability of the solutions obtained according to (a) to (d) is tested as described under A.

The following values were found:

| Experiment | Available iodine content [%] | Loss of iodine in 15 hours at 80° C. [%] |
|---|---|---|
| a | 2.05 | 28 |

-continued

| Experiment | Available iodine content [%] | Loss of iodine in 15 hours at 80° C. [%] |
|---|---|---|
| b | 2.05 | 15.4 |
| c | 2.07 | 12.0 |
| d | 2.02 | 6.0 |

Comparison with the values for the stability of the PVP-iodine solutions given under A shows that the solutions obtained according to B are more stable by a factor of from about 2 to 4. However, they do not attain the stability of a PVP-iodine solution prepared from solid PVP-iodine.

C. 80 parts of isopropanol and 40 parts of a mixture of 350 parts of vinylpyrrolidone, 70 parts of isopropanol and 1.75 parts of di-tertiary butyl peroxide are first introduced into a stirred pressure autoclave. The charge is then heated to 120° C., which results in a gauge pressure of 2.5 bars, and the remainder of the mixture is then metered into the autoclave in the course of 3 hours. The polymerization is then continued for a further 3 hours, until the residual content of monomeric vinylpyrrolidone has fallen to less than 0.5%. The batch is cooled and then diluted to 20% strength with 1,250 parts of water. The K value of the polymer thus obtained is 31.5.

The solution is divided into 4 parts and is converted to PVP-iodine solutions as described under B.

The stability of the resulting PVP-iodine solutions is tested as described in A.

The following values were found:

| Experiment | Available iodine content [%] | Loss of iodine in 15 hours at 80° C. [%] |
|---|---|---|
| a | 2.08 | 19 |
| b | 2.1 | 1.9 |
| c | 2.15 | 2.1 |
| d | 2.15 | 2.0 |

The loss of iodine has been reduced throughout compared to the values under A and B. The values under b, c and d are particularly outstanding. After the treatment with steam, there is virtually no longer any difference between the various products. The solutions obtained are equivalent in stability to a solution prepared from solid PVP-iodine.

EXAMPLE 2

300 parts of a mixture of 300 parts of vinylpyrrolidone, 700 parts of isopropanol and 12 parts of di-tertiary butyl peroxide are first introduced into a stirred pressure autoclave and heated to 145° C., resulting in a gauge pressure of about 7.5 bars in the apparatus. The remaining mixture is then metered in uniformly in the course of 3 hours. Heating is then continued for 1 hour until the residual content of monomeric vinylpyrrolidone is less than 0.5%. The mixture is now cooled to 80° C. by letting-down, and at the same time about 570 parts of isopropanol are distilled off. The mixture is then diluted with 100 parts of water and the isopropanol is distilled off completely by passing steam into the mixture. When the temperature at which the vapor passes over has reached 98°, the mixture is flushed with a further 90 parts of steam. The solids content of the solution is then brought to 40% with water. The K value of the PVP is 12.5.

The solution is divided into 3 parts which are then converted into aqueous PVP-iodine solutions as follows.

(a) 206 parts of the PVP solution are mixed with 6.5 parts of potassium iodide dissolved in 26.5 parts of water, and 11 parts of ground iodine are then added with vigorous stirring. After 6 hours' stirring, the solution is homogeneous.

(b) The solution is converted by spray drying into a powder containing 8.0% of water. A 40% strength solution in water is then again prepared and is treated further as described under Example a.

(c) The solution is spray-dried as described under (b). 92.4 parts of the solid product obtained, containing 8.0% of water, are mixed with 15 parts of ground iodine in a tumbler mixer for 6 hours and then heated for 20 hours at 75° C. A solution is prepared by adding 143 parts of water.

(d) For comparison, a commercial PVP, manufactured according to German Pat. No. 922,378 and having a K value of 17, is dissolved in water to give a 40% strength solution, which is reacted as described under (a) to give a PVP-iodine solution.

The stability of the PVP-iodine solutions prepared according to Example (a) to (d) is tested as described in Example 1.

The following values were found:

| Experiment | Available iodine content [%] | Loss of iodine in 15 hours at 80° C. [%] |
|---|---|---|
| a | 4.2 | 18.4 |
| b | 4.2 | 14.5 |
| c | 4.4 | 15.1 |
| d | 4.0 | 60.2 |

As may be seen from the Table, the stability of an aqueous solution of the PVP-iodine formulations of the invention is clearly superior to that of a PVP-iodine prepared from commercial PVP of K value 17.

EXAMPLE 3

385 parts of isopropanol, 30 parts of vinylpyrrolidone and 1.2 parts of di-tert.-butyl peroxide are first introduced into a stirred pressure autoclave and after heating the charge to 175° C. and bringing the pressure to about 14 bars, a mixture of 315 parts of isopropanol, 270 parts of vinylpyrrolidone and 10.8 parts of di-tert.-butyl peroxide is introduced in the course of 4 hours. The mixture is then heated for a further hour, until the residual content of vinylpyrrolidone is less than 0.5%. It is then cooled to 80° C. by letting down, and at the same time 630 parts of isopropanol are distilled off. The mixture is then diluted with 50 parts of water and the isopropanol is distilled off completely by passing steam into the mixture. When the temperature at which the vapor passes over has reached 98° C., the mixture is flushed with a further 300 parts of steam. The solids content of the solution is then brought to 60% with water. The K value of the PVP is 10.6.

The solution is divided into 3 parts which are then converted into aqueous PVP-iodine solutions as follows.

(a) 206 parts of the PVP solution are mixed with 23 parts of potassium iodide dissolved in 86 parts of water, and 35 parts of ground iodine are then added with vigorous stirring. After 6 hours' stirring, the solution is homogeneous.

(b) The solution is converted by spray drying into a powder containing 8.0% of water. A 60% strength solution in water is then again prepared and is treated further as described under Example (a).

(c) The solution is spray-dried as under (b). 76 parts of the solid product obtained, containing 8% of water, are mixed with 30 parts of ground iodine in a tumbler mixer for 6 hours and then heated for 30 hours at 65° C. A solution is prepared by adding 94 parts of water.

(d) For comparison, a commercial PVP, manufactured according to German Pat. No. 922,378 and having a K value of 17, is dissolved in water to give a 60% strength solution, which is reacted as described under (a) to give a PVP-iodine solution.

The stability of the PVP-iodine solutions prepared according to Example (a) to (d) is tested as described in Example 1.

The following values were found:

| Experiment | Available iodine content [%] | Loss of iodine in 15 hours at 80° C. [%] |
|---|---|---|
| a | 9.8 | 22.3 |
| b | 9.9 | 17.5 |
| c | 10.2 | 18.5 |
| d | 9.4 | 66.5 |

As may be seen from the Table, the stability of an aqueous solution of the PVP-iodine formulations of the invention is clearly superior to that of a PVP-iodine prepared from commercial PVP of K value 17.

EXAMPLE 4

300 parts of a mixture of 300 parts of vinylpyrrolidone, 700 parts of isopropanol and 12 parts of di-tertiary butyl peroxide are first introduced into a stirred pressure autoclave and heated to 125° C., resulting in a gauge pressure of about 4 bars in the apparatus. The remaining mixture is then metered in uniformly in the course of 3 hours. Heating is then continued for 1 hour until the residual content of monomeric vinylpyrrolidone is less than 0.5%.

The mixture is now cooled to 80° C. by letting-down, and at the same time about 500 parts of isopropanol are distilled off. The mixture is now diluted with 100 parts of water and the isopropanol is distilled off completely by passing steam into the mixture. When the temperature at which the vapor passes over has reached 98°, the mixture is flushed with a further 90 parts of steam. The solids content of the solution is then brought to 40% with water. The K value of the PVP is 16.6.

The solution is divided into 3 parts which are then converted into aqueous PVP-iodine solutions as follows.

(a) 206 parts of the PVP solution are mixed with 6.5 parts of potassium iodide dissolved in 26.5 parts of water, and 11 parts of ground iodine are then added with vigorous stirring. After 6 hours' stirring, the solution is homogeneous.

(b) The solution is converted by spray drying into a powder containing 8.0% of water. A 40% strength solution in water is then again prepared and is treated further as described under Example a.

(c) The solution is spray-dried as described under (b). 92.4 parts of the solid product obtained, containing 8.0% of water, are mixed with 15 parts of ground iodine in a tumbler mixer for 6 hours and then heated for 20 hours at 85° C. A solution is prepared by adding 143 parts of water.

(d) For comparison, a commercial PVP, manufactured according to German Pat. No. 922,378 and having a K value of 17, is dissolved in water to give a 40% strength solution, which is reacted as described under (a) to give a PVP-iodine solution.

The stability of the PVP-iodine solutions prepared according to Examples (a) to (d) is tested as described in Example 1.

The following values were found:

| Experiment | Available iodine content [%] | Loss of iodine in 15 hours at 80° C. [%] |
|---|---|---|
| a | 4.3 | 9.5 |
| b | 4.3 | 8.5 |
| c | 4.3 | 8.5 |
| d | 4.0 | 60.2 |

As may be seen from the Table, the stability of an aqueous solution of the PVP-iodine formulation of the invention is clearly superior to that of a PVP-iodine prepared from commercial PVP of K value 17.

EXAMPLE 5

300 parts of a mixture of 300 parts of vinylpyrrolidone, 700 parts of isopropanol and 12 parts of di-tertiary butyl peroxide are first introduced into a stirred pressure autoclave and heated to 115° C., resulting in a gauge pressure of about 3 bars in the apparatus. The remaining mixture is then metered in uniformly in the course of 3 hours. Heating is then continued for 1 hour until the residual content of monomeric vinylpyrrolidone is less than 0.5%.

The mixture is now cooled to 80° C. by letting-down, and at the same time about 350 parts of isopropanol are distilled off. The mixture is now diluted with 100 parts of water and the isopropanol is distilled off completely by passing steam into the mixture. When the temperature at which the vapor passes over has reached 98°, the mixture is flushed with a further 90 parts of steam. The solids content of the solution is then brought to 40% with water. The K value of the PVP is 20.1.

The solution is divided into 3 parts which are then converted into aqueous PVP-iodine solutions as follows.

(a) 206 parts of the PVP solution are mixed with 6.5 parts of potassium iodide dissolved in 26.5 parts of water, and 11 parts of ground iodine are then added with vigorous stirring. After 6 hours' stirring, the solution is homogeneous.

(b) The solution is converted by spray drying into a powder containing 8.0% of water. A 40% strength solution in water is then again prepared and is treated further as described under Example a.

(c) The solution is spray-dried as described under (b). 92.4 parts of the solid product obtained, containing 8.0% of water, are mixed with 15 parts of ground iodine in a tumbler mixer for 6 hours and then heated for 20 hours at 90° C. A solution is prepared by adding 143 parts of water.

(d) For comparison, a commercial PVP, manufactured according to German Pat. No. 922,378 and having a K value of 17, is dissolved in water to give a 40% strength solution, which is reacted as described under (a) to give a PVP-iodine solution.

The stability of the PVP-iodine solutions prepared according to Examples (a) to (d) is tested as described in Example 1.

The following values were found:

| Experiment | Available iodine content [%] | Loss of iodine in 15 hours at 80° C. [%] |
|---|---|---|
| a | 4.2 | 6.5 |
| b | 4.2 | 6.5 |
| c | 4.3 | 7.5 |
| d | 4.0 | 60.2 |

As may be seen from the Table, the stability of an aqueous solution of the PVP-iodine formulation of the invention is clearly superior to that of a PVP-iodine prepared from commercial PVP of K value 17.

EXAMPLE 6

1,000 parts of vinylpyrrolidone, 428 parts of isopropanol and 10 parts of tertiary butyl hydroperoxide are heated to the boil in a stirred vessel fitted with a reflux condenser. After the boiling point of about 96° C. has been reached, 0.5 part of an 0.1% strength solution of copper acetate in isopropanol is added and the mixture is heated until the residual content of monomeric vinylpyrrolidone is less than 0.5%, based on PVP. The mixture is then diluted with 951 parts of water and the isopropanol is driven off by passing steam into the mixture. When the temperature at which the vapor passes over has reached 98°, the mixture is flushed with a further 1,000 parts of steam. A powder containing 4% of water is then isolated by spray drying. The K value of the product is 32. For the further reaction, a 15% strength aqueous solution is again prepared from the pulverulent PVP.

850 parts of the 15% strength solution of the PVP of K value 32 and 150 parts of an aqueous 19.85% strength potassium iodide solution are mixed in a stirred vessel. The mixture is divided into 5 equal portions. 200 part portions are mixed with the various amounts of 30% strength aqueous hydrogen peroxide solution and concentrated citric acid shown in the Table below, and then made up to 220 parts with water. After mixing for 2 hours, the solutions are examined. The iodine content and the iodine loss are determined as described under 1A.

| No. | 30% strength hydrogen peroxide parts | % of theory | citric acid | pH | Available iodine content of the solution found % | theory % | Loss of iodine in aqueous solution |
|---|---|---|---|---|---|---|---|
| 1 | 1.0 | 50 | 5.5 parts | 4.0 | 1.0 | 1.08 | 22% |
| 2 | 1.34 | 67 | 8.5 parts | 4.0 | 1.4 | 1.45 | 17.2% |
| 3 | 2.0 | 100 | 8.5 parts | 4.0 | 1.65 | 2.17 | 10.9% |
| 4 | 3.0 | 150 | 10.5 parts | 4.0 | 1.7 | 2.17 | 10.2% |
| 5 | 4.0 | 200 | 15.0 parts | 3.8 | 1.7 | 2.17 | 8.3% |

As can be seen from the Table, the content of available iodine increases with increasing amount of hydrogen peroxide, without reaching the theoretical value. The loss of iodine decreases with increasing amount of hydrogen peroxide.

EXAMPLE 7

750 parts of a 15% strength solution of PVP of K value 32, as described in Example 3, and 250 parts of a 19.85% strength potassium iodide solution are mixed. 200 part portions of the mixture are mixed with various amounts of 30% strength hydrogen peroxide and concentrated phosphoric acid as shown in the Table, and then made up to 220 parts with water.

| No. | Hydrogen peroxide parts | % of theory | Concentrated phosphoric acid parts | pH | Available iodine content of the solution found, [%] | theory, [%] | Loss of iodine in aqueous solution |
|---|---|---|---|---|---|---|---|
| 1 | 1.67 | 50 | 5.0 | 4.0 | 1.7 | 1.7 | 12.7 |
| 2 | 2.22 | 67 | 6.4 | 4.0 | 2.0 | 2.3 | 9.2 |
| 3 | 3.34 | 100 | 8.4 | 4.0 | 2.3 | 3.4 | 5.0 |
| 4 | 5.00 | 150 | 8.6 | 3.9 | 2.4 | 3.4 | 4.6 |
| 5 | 6.68 | 200 | 11.5 | 3.7 | 2.7 | 3.4 | 3.8 |

It can be seen from the Tables of Examples 3 and 4 that with increasing amount of hydrogen peroxide the content of available iodine also increases, but without reaching the theoretical value. Here again, as is also shown in Example 3, the loss of iodine decreases with increasing amount of hydrogen peroxide.

EXAMPLE 8

66.5 parts of the polyvinylpyrrolidone which has been polymerized and dried in accordance with Example 3, and has a K value of 32 and contains 4% of water, and 14.7 parts of potassium iodide are dissolved in 418.8 parts of water in a stirred flask. 100 part portions of the solution are mixed with the amounts of glacial acid shown in the Table which follows. 1 part of 30% strength hydrogen peroxide (=1 equivalent, based on potassium iodide), is then added to each mixture and thoroughly mixed in, and after standing for 20 hours and 90 hours, the pH and the content of available iodine are determined.

| Experiment No. | Glacial acetic acid parts | Theoretical content of available iodine in the solution, calculated from the oxidizing agent [%] | after 20 hours at room temperature | | after 90 hours at room temperature | |
|---|---|---|---|---|---|---|
| | | | pH | content of available iodine in solution [%] | % of theory | pH | content of available iodine in solution [%] | % of theory |
| 1 | 0.4 | 2.21 | 6.9 | 0.885 | 40.0 | 6.2 | 0.880 | 39.9 |
| 2 | 1.2 | 2.20 | 5.7 | 1.89 | 85.9 | 5.5 | 1.92 | 87.2 |
| 3 | 4.8 | 2.15 | 4.8 | 1.91 | 88.8 | 4.7 | 1.92 | 89.2 |

| Experiment No. | Glacial acetic acid parts | Theoretical content of available iodine in the solution, calculated from the oxidizing agent [%] | after 20 hours at room temperature | | | after 90 hours at room temperature | | |
|---|---|---|---|---|---|---|---|---|
| | | | | content of available iodine | | | content of available iodine | |
| | | | pH | in solution [%] | % of theory | pH | in solution [%] | % of theory |
| 4 | 12.8 | 1.97 | 4.2 | 1.79 | 90.8 | 4.0 | 1.84 | 93.3 |

With increasing amount of glacial acetic acid, the pH of the solution drops and the conversion from iodide ions to free iodine increases.

EXAMPLE 9

The oxidizing agent solutions shown in the Table which follows (=100% of the amount theoretically required for complete oxidation of the potassium iodide) are added to 104 part portions of a solution of 66.5 parts of the polyvinylpyrrolidone which has been polymerized and dried in accordance with Example 3 (K value=32, water content=4%), 14.7 parts of potassium iodide and 20 parts of phosphoric acid in 418.8 parts of water, and are thoroughly mixed in. The pH, and the content of available iodine, are determined after standing for 3 hours and for 68 hours.

the charge to 140° C. and bringing the pressure to 7 bars, a mixture of 315 parts of isopropanol, 270 parts of vinylpyrrolidone and 10.8 parts of di-tert.-butyl peroxide is introduced in the course of 2.75 hours. Polymerization is then continued for a further 3 hours, until the monomer content has fallen to below 0.5%. The mixture is then cooled to 80° C. by letting down, and at the same time 530 parts of isopropanol are distilled off. The mixture is then diluted with 100 parts of water and the isopropanol is distilled off completely by passing steam into the mixture. When the temperature at which the vapor passes over has reached 98° C., the mixture is flushed with a further 300 parts of steam. The solids content of the solution is then brought to 30% with water. The K value of the PVP is 12.5.

The PVP solution is divided into 3 equal portions

| Experiment No. | Oxidizing agent | Theoretical content of available iodine in the solution, calculated from the oxidizing agent [%] | after 3 hours | | | after 68 hours | | |
|---|---|---|---|---|---|---|---|---|
| | | | | content of available iodine | | | content of available iodine | |
| | | | pH | in solution [%] | % of theory | pH | in solution [%] | % of theory |
| 1 | 0.76 part of potassium iodate dissolved in 100 parts of water | 1.325 | 2.8 | 1.315 | 99.2 | 2.8 | 1.325 | 100 |
| 2 | 2.4 parts of potassium persulfate dissolved in 10 parts of water | 1.93 | 2.1 | 1.48 | 76.7 | 2.1 | 1.53 | 79.3 |
| 3 | 0.8 part of tertiary butyl hydroperoxide dispersed in 10 parts of water | 1.96 | 3.1 | 0.87 | 44.3 | 2.6 | 1.49 | 76 |
| 3a | 0.8 part of tertiary butyl hydroperoxide dispersed in 10 parts of water + 0.75 part of an 0.01% strength solution of copper chloride in water | 1.96 | 3.0 | 1.08 | 55.2 | 2.9 | 1.51 | 77 |

In Experiment 3a, the copper chloride solution was added immediately after adding the oxidizing agent.

Whilst with potassium iodate the theoretical iodine value is reached immediately after addition, the percompounds have a markedly slower effect and furthermore do not reach the theoretical iodine value.

EXAMPLE 10

385 parts of isopropanol, 30 parts of vinylpyrrolidone and 1.2 parts of di-tert.-butyl peroxide are first introduced into a stirred pressure reactor and after heating each of 333 parts and the amount of sodium iodide shown in the Table which follows is dissolved therein. Thereafter phosphoric acid and hydrogen peroxide are added, in the stated sequence, as shown in the Table which follows, and the mixtures are made up to 500 parts with water. After mixing for 2 hours, the solutions are examined. The iodine content and the loss of iodine are determined as described under 1A.

| No. | NaI (parts) | Concentrated phosphoric acid (parts) | 30% strength H$_2$O$_2$ (parts) = ⅔ of theory | pH | Available iodine content of the solution | | Loss of iodine in aqueous solution |
| --- | --- | --- | --- | --- | --- | --- | --- |
| | | | | | found % | theory % | |
| a | 20.85 | 30 | 15.7 | 4.3 | 2.20 | 2.35 | 14.5% |
| b | 34.3 | 50 | 25.9 | 4.4 | 3.65 | 3.87 | 15.6% |
| c | 50.6 | 70 | 38.4 | 4.4 | 5.35 | 5.72 | 17.1% |

We claim:

1. A process for the preparation of a stable aqueous solution of PVP-iodine which comprises:
   mixing in an aqueous medium,
   (a) PVP as an aqueous solution of from 10 to 60% strength by weight, wherein said PVP has a K value of from 8 to 50 and has been prepared in the form of an aqueous solution by the steps of
   (1) polymerizing vinylpyrrolidone in an organic solvent which is an aromatic hydrocarbon or a lower aliphatic monohydric alcohol of 1 to 4 carbon atoms at a concentration of monomer of from 10 to 80% by weight and in the presence of a free radical initiator which is an organic percompound selected from the group consisting of alkyl hydroperoxides and dialkyl peroxides of 1 to 8 carbon atoms per alkyl and per esters in an amount of about 0.1 to 5% by weight, based on vinylpyrrolidone,
   (2) mixing the resulting solution of PVP in the organic solvent with water,
   (3) distilling off the organic solvent to give an aqueous solution of PVP, and
   (4) treating the aqueous solution of PVP with steam in the amount of from 20 to 200% of steam based on the weight of PVP; with
   (b) iodine in an amount of from 5 to 60% by weight, based on PVP;
   and with
   (c) a compound which provides iodide ions in an amount of from 10 to 200% by weight, calculated as iodide ions and based on the amount of iodine employed.

2. The process of claim 1, wherein a PVP which has been produced by polymerization in the presence of a dialkyl peroxide as the organic initiator is used.

3. The process of claim 1, wherein the polymer solution obtained from the polymerization is employed directly, after dilution with water, for the preparation of the aqueous PVP-iodine solution.

4. The process of claim 1, wherein the polymer solution first obtained from the polymerization is subjected to a steam distillation.

5. The process of claim 1, wherein sodium iodide or potassium iodide is used as the compound which provides iodide ions.

6. The process of claim 1, wherein a solution of PVP and of the compound which provides iodide ions is first prepared, to which the iodine is then added.

7. The process of claim 1, wherein the free iodine is produced in the solution, from the compound which provides iodide ions and is present in excess, by reaction with an oxidizing agent.

8. The process of claim 7, wherein hydrogen peroxide is used as the oxidizing agent.

9. The process of claim 1, wherein the polymerization of vinylpyrrolidone takes place in the presence of from 0.01 to 10 ppm of a complex compound of a heavy metal of atomic number from 23 to 29 or its salt with an organic acid.

10. The process of claim 1, wherein the pH of the aqueous solution of PVP and iodine is from 2 to 7.

11. The process of claim 1, wherein the organic solvent is toluene.

* * * * *